United States Patent [19]
McGrath

[11] Patent Number: 5,877,222
[45] Date of Patent: *Mar. 2, 1999

[54] METHOD FOR TREATING AIDS-ASSOCIATED DEMENTIA

[75] Inventor: Michael S. McGrath, Burlingame, Calif.

[73] Assignee: The Regents of the University of California, Oakland, Calif.

[ * ] Notice: This patent issued on a continued prosecution application filed under 37 CFR 1.53(d), and is subject to the twenty year patent term provisions of 35 U.S.C. 154(a)(2).

[21] Appl. No.: 684,460

[22] Filed: Jul. 19, 1996

[51] Int. Cl.⁶ .................................................. A61K 31/13
[52] U.S. Cl. ............................................................. 514/661
[58] Field of Search ............................................. 424/661

[56] References Cited

U.S. PATENT DOCUMENTS

| | | | |
|---|---|---|---|
| 4,507,285 | 3/1985 | Kuhne | 424/130 |
| 4,725,437 | 2/1988 | Kuhne | 424/130 |
| 4,851,222 | 7/1989 | Kuhne et al. | 424/661 |
| 4,880,638 | 11/1989 | Gordon | 424/662 |
| 5,580,860 | 12/1996 | Kojima et al. | 514/45 |

OTHER PUBLICATIONS

Busch et al. 10th International Conf. on Aids: Yokahama–Shi, Japan, Abstract P80245, 1994.
Yarchoan, et al., Lancet, V1, pp. 132–135 (abstract), 1987.
Anonymous, American Pharmacy, VNS27, p. 14(abstract), 1987.
Routy et al., Lancet V336, p. 248(abstract), 1990.
Portegies, Drugs (New Zealand), V49, (Suppl 1) pp. 25–31(abstract), 1995.

*Primary Examiner*—Raymond J. Henley, III
*Attorney, Agent, or Firm*—Crosby, Heafey, Roach & May

[57] ABSTRACT

The invention comprises inhibiting expression of TNF-α by administering an effective amount of a stabilized activated oxygen in a matrix of chlorite ions. Preferably, a pharmaceutically acceptable formulation of tetrachlorodecaoxide is used, and more preferably, WF-10. An effective amount of WF-10 comprises up to about 0.5 ml/kg. Another embodiment of the invention is a method of treating AIDS-associated dementia comprising the step of administering to a human an amount of a stabilized activated oxygen in a matrix of chlorite ions sufficient to inhibit production of TNF-α.

4 Claims, 3 Drawing Sheets

METHOD FOR TREATING AIDS-ASSOCIATED DEMENTIA

FIELD OF THE INVENTION

The invention relates to the field of treating immune system diseases and more particularly to the treatment of AIDS dementia by inhibiting production of tumor necrosis factor.

BACKGROUND OF THE INVENTION

HIV infection causes a broad range of pathologic processes. One of the most important late stage complications of HIV infection is known as AIDS dementia complex or HIV-associated encephalitis. This is a pathologic process that is characterized by frank memory loss, social withdrawal, alterations in personality and the inability to perform normal daily living activities.

The pathologic processes that characterize AIDS dementia include astrocytosis (thought in part to be secondary to factors causing toxic damage to the brain), multinucleated giant cell formation, microglial nodule formation, and frank neural cell death. All of these changes are seen in the context of HIV-infected macrophage infiltration both perivascularly as well as into the brain parenchyma. In certain studies, the frequency of the HIV-expressing macrophage was associated with the degree of dementia. Virtually all patients with advanced dementia have extremely high levels of HIV in the brain, and this virus is almost always associated with brain macrophages or microglial cells as neuron and astrocytes have rarely, if ever, been documented as being infected in-vivo by HIV.

Although the mechanism by which HIV causes dementia is unclear, many studies implicate macrophages as playing a pivotal role in the dementia process through the elaboration of neurotoxic substances. One of the principal substances implicated in the pathogenesis of AIDS dementia is tumor necrosis factor (TNF-α). Macrophages release TNF-α and other cytokines in response to stimulus of the immune system. It is a critical component of the cell mediated immune response to infections. TNF-α is expressed in response to bacterial and viral immunostimulators, and particularly in response to HIV infections, and has been shown to cause damage to brain cells in vitro.

TNF-α also manifests a dose dependent toxicity in other tissues. At chronic levels, TNF-α can cause cachexia and at acute levels can cause septic shock. Prior art methods for suppressing TNF-α rely on antiinflammatory and immunosuppressive steroids. However, such steroids also suppress other cytokines necessary for proper cell mediated response.

The prior art offers no treatment for patients suffering from AIDS dementia. Since dementia affects 20%-30% of AIDS patients, there is a substantial need for an effective treatment. Furthermore, there is a need for controlling TNF-α levels while minimizing the effects on other cytokines. This invention satisfies these and other needs.

SUMMARY OF THE INVENTION

A method for inhibiting expression of TNF-α comprising the step of administering to a human an effective amount of a stabilized activated oxygen in a matrix of chlorite ions. Preferably, the step of administering a stabilized activated oxygen comprises administering a pharmaceutically acceptable formulation of tetrachlorodecaoxide and more preferably comprises administering WF-10. An effective amount of WF-10 comprises up to about 0.5 ml/kg. Another embodiment of the invention is a method of treating AIDS-associated dementia comprising the step of administering to a human an amount of a stabilized activated oxygen in a matrix of chlorite ions sufficient to inhibit production of TNF-α.

DETAILED DESCRIPTION OF THE INVENTION

AIDS Dementia Monocytes

Figure 1:
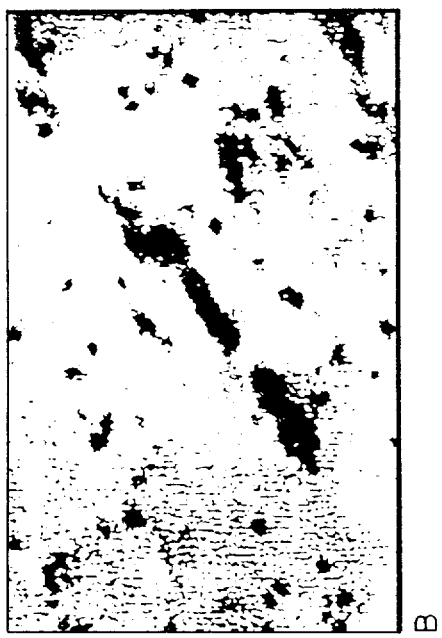
FIG. 1 illustrates an immunohistochemical analysis of a brain specimen from a patient with AIDS-associated dementia, stained with anti-CD14, anti-HIV p24, anti-PDGF-B or anti-PDGF-B receptor antibodies in Frames A, B, C and D respectively.
Figure 1:
Figure 1:
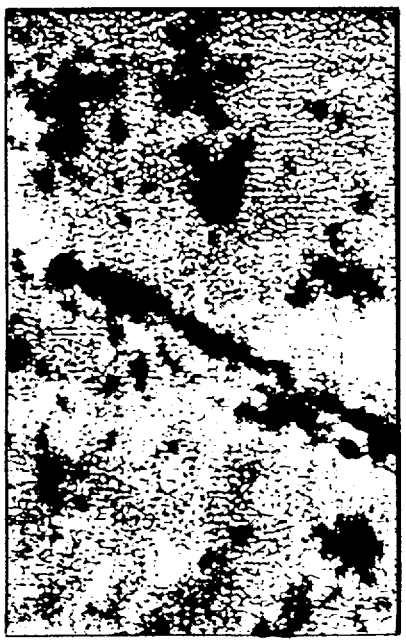
Figure 1:

Studies on peripheral blood mononuclear cells from a wide variety of HIV-infected patients, including those with dementia, indicate that patients exhibiting AIDS-associated dementia have a distinct population of circulating monocytes. Standard Ficoll-hypaque separation techniques gave lower yields of monocytes from demented patients as compared to HIV-infected control patients (44% vs. 67% respectively). The percent yield was calculated based on determining the number of CD14 expressing cells in whole blood in comparison to the yield of CD14 expressing cells after Ficoll separation. Several of the demented patient yields were less than 10% the predicted yield.

The decreased yield from Ficoll separation suggests that a subset of monocytes from demented patients might be more dense than control patients. A further analysis employed Percoll gradient separation in an attempt to retrieve the monocytes lost in the Ficoll gradient. Table I shows the actual recovery of monocytes at the density normally used for Ficoll separation (1.077 g/ml) as compared to a higher density created by the Percoll gradient (1.077–1.087 g/ml).

A two phase step-gradient of Percoll (Sigma, St. Louis Mo.) was prepared in 15 ml conical centrifuge tubes as follows: a bottom layer of 4.5 ml 1.087 density Percoll and an upper layer of 4.5 ml of 1.077 density Percoll. 1.5 ml of whole heparinized blood was mixed with an equal volume of isotonic saline. The blood/saline mixture was then gently layered over the Percoll step-gradient and centrifuged for 20 min, RT, at 800×g. Cells from 1.077 and 1.087 liquid interfaces were collected and washed in 5 volumes of RPMI 1640 (spin at 400×g, 5 min, discard supernatants). Cell pellets were re-suspended in RPMI 1640 with 10% fetal bovine serum and counted by hemacytometer. The percent of CD14 expressing cells was determined by whole blood staining with fluorosinated anti-CD14 antibodies. After Percoll gradient separation the percent of CD14 stained cells was calculated and is expressed in the far column.

TABLE 1

CD14 Recovery From 2 Step Percoll Gradient

| | % CD14 Whole Blood | Density <1.077 | Density 1.077–1.087 | % CD14 in Dense Fraction |
|---|---|---|---|---|
| Normal | | | | |
| HL | 6.2% | $16 \times 10^4$ | $6.3 \times 10^3$ | 4% |
| MM | 5.4% | $25 \times 10^4$ | $3.4 \times 10^3$ | 12% |
| MS | 6.4% | $15.2 \times 10^4$ | $9 \times 10^3$ | 5.6% |
| HIV > 200 | | | | |
| 8508 | 5.6% | $26 \times 10^4$ | $12.6 \times 10^3$ | 4% |
| 3958 | 5.6% | $24 \times 10^4$ | $6.6 \times 10^3$ | 3% |

TABLE 1-continued

CD14 Recovery From 2 Step Percoll Gradient

| | % CD14 Whole Blood | Density <1.077 | Density 1.077–1.087 | % CD14 in Dense Fraction |
|---|---|---|---|---|
| HIV < 200 | | | | |
| St | 5.2% | $5.3 \times 10^4$ | $12.6 \times 10^3$ | 18% |
| Sa | 1.8% | $8.4 \times 10^3$ | $4.6 \times 10^3$ | 35% |
| 571 | 3.2% | $35 \times 10^3$ | $6 \times 10^3$ | 15% |
| 2393 | 4.2% | $12.6 \times 10^4$ | $8.8 \times 10^3$ | 0.6% |
| HIV Dementia | | | | |
| a | 10.9% | $29.6 \times 10^3$ | $11 \times 10^3$ | 27% |
| U | 7.4% | $10.2 \times 10^4$ | $19 \times 10^3$ | 16% |
| T | 7.8% | $7 \times 10^3$ | $9 \times 10^3$ | 56% |
| S | 4.4% | $35 \times 10^3$ | $35 \times 10^3$ | 50% |

Very few dense monocytes were found in control and HIV patients with greater than 200 CD4 cells/μl specimens. An increased frequency of dense monocytes was found in patients with less than 200 CD4 cells/μl. The highest frequency of dense monocytes was in patients with AIDS-associated dementia. These results indicate that there are relatively more dense monocytes in patients with advanced HIV disease, particularly in patients with dementia.

Density was also measured by flow cytometric analysis of the degree of granularity of PBMC's from a series of HIV-infected patients, control patients, and patients with dementia. Forward-angle light scatter analysis between different populations of monocytes was essentially the same, suggesting that the overall size of monocytes between the various groups was the same. However, there is a significant side scatter increase in monocytes from patients with less than 200 CD4 cells and dementia as compared to control patients and those with greater than 200 CD4 cells. As shown in Table 2, there is a continuum from normal granularity to intermittently high granularity in patients with less than 200 CD4 cells to the highest granularity in monocytes from patients with AIDS-associated dementia. All values shown in Table 2 represent light scatter units of CD14+ cells.

TABLE 2

Median Side Scatter Values For CD14 Cells (Whole Blood)

| Normal | | HIV CD4 > 200 | | HIV CD4 < 200 | | HIV Dementia | |
|---|---|---|---|---|---|---|---|
| MS | 346 | 01201 | 405 | 1478 | 478 | a | 403 |
| RG | 364 | 01202 | 311 | 0597 | 386 | B | 382 |
| VN | 314 | 01203 | 333 | 5716 | 369 | G | 526 |
| MW | 271 | 01205 | 357 | 6202 | 370 | H | 354 |
| HL | 402 | 01101 | 349 | 4947 | 431 | I | 333 |
| KM | 373 | 01102 | 374 | St | 343 | J | 426 |
| RW | 324 | 01103 | 342 | 8912 | 332 | N | 439 |
| MM | 366 | 01106 | 325 | 6499 | 404 | O | 378 |
| DA | 333 | 01107 | 321 | 2393 | 527 | P | 436 |
| RA | 374 | 01108 | 333 | 571 | 429 | Q | 439 |
| | | 01109 | 318 | 572 | 427 | R | 723 |
| n = 10 | | | | La | 343 | EW | 689 |
| Median = 347 ± 38 | | n = 11 | | Su | 340 | K | 470 |
| | | median = 343 ± 28 | | 573 | 441 | S | 403 |
| | | | | 574 | 445 | T | 351 |
| | | | | | | U | 375 |
| | | | | n = 15 | | | |
| | | | | median = 404 ± 57 | | n = 16 | |
| | | | | | | median = 445 ± 113 | |

Macrophages in the brain of patients with AIDS dementia are commonly seen in a perivascular pattern. FIG. 1 shows an immunohistochemical analysis of a brain specimen from a patient with AIDS dementia. Frame A shows staining with anti-CD14, an antibody specific to macrophages. These macrophages are activated and express various cytokines, including TNF-α. Due to the perivascular nature of these cells, the blood monocytes may cross the blood/brain barrier and give rise to the perivascular and ultimately parenchymal macrophages seen in the brains of patients with AIDS dementia. Table 3 shows that monocytes with increased granularity express TNF-α.

Monocytes from six demented patients were stained with anti-CD14 and through a fixation and solubilization step, were stained with a second antibody to TNF-α. Cytoplasmic staining was performed and cells exposed to facs-juice (Becton-Dickinson, San Jose). The percent of TNF+ cells was calculated, as were the median side and forward scatter of the CD14-expressing cells. The percent of TNF-expressing cells in the demented patients is compared with the percentage of TNF+ cells in two normal specimens.

TABLE 3

TNF-α Expression and Scatter Profile of CD14+ Cells From Whole Blood

| Patient | CD14/ % TNF+ | CD14/TNF+ Median SSC | Median FSC | CD14/TNF− Median SSC | Median FSC |
|---|---|---|---|---|---|
| a | 10 | 491 | 794 | 232 | 480 |
| U | 42 | 1024 | 590 | 309 | 557 |
| V | 26 | 381 | 656 | 269 | 481 |
| W | 65 | 709 | 476 | 253 | 522 |
| X | 15 | 422 | 663 | 248 | 503 |
| T | 45 | 347 | 683 | 229 | 97 |
| mean= | | 562 ± 260 | 644 ± 106 | 257 ± 30 | 507 ± 29 |
| Normals | | | | | |
| RG | 4 | | | | |
| RM | 2 | | | | |

Comparison of the light scatter of TNF-expressing to non-expressing cells shows that the larger, more granular cells were exclusively those that expressed TNF-α. Monocytes that did not express TNF-α were uniformly small. Therefore, patients with AIDS-associated dementia have circulating, activated monocytes that express TNF-α without additional stimulus. Increased granularity, TNF-expressing monocytes are found in patients with advanced AIDS (CD4<200 cells/ml) as well as in patients with dementia, indicating that the abnormally activated monocytes exist prior to the development of clinical AIDS-associated dementia.

Further, as shown in Table 4, monocytes from patients with AIDS-associated dementia are characterized by high expression of cell surface marker CD69. Monocytes from patients with AIDS-associated dementia have a significantly higher percentage of cells that are CD69+ than patients with advanced stages of AIDS (CD4<200 cells/ml) or controls.

TABLE 4

Percentage of CD14 Cells That Are CD69+

| HIV Dementia | | HIV CD4 < 200 | | Normals | |
|---|---|---|---|---|---|
| a | 46 | 1 | 8 | RG | 4 |
| U | 96 | 2 | 6 | NA | 4 |
| V | 72 | 3 | 34 | | |
| W | 76 | 4 | 21 | | |
| X | 80 | 5 | 3 | | |
| T | 30 | 6 | 8 | | |
| VC | 49 | 7 | 9 | | |
| mean = 64 ± 23 | | mean = 13 ± 11 | | | |

Like TNF-expression, table 5 shows that monocytes expressing CD69 are more dense and have greater granularity than those that do not. The percent of CD69+ cells was calculated as were the median side and forward scatter of the CD14-expressing cells.

TABLE 5

CD69 Expression and Scatter Profile of CD14+ Cells

| Patient | % CD69+ of CD14+ | All CD14 cells median | | CD14+/CD69+ median | | CD14+/CD69− median | |
|---|---|---|---|---|---|---|---|
| | | FSC | SSC | FSC | SSC | FSC | SSC |
| a | 46 | 652 | 419 | 817 | 537 | 629 | 353 |
| U | 96 | >1000 | >1000 | >1000 | >1000 | * | * |
| V | 72 | 777 | 626 | 827 | 749 | 627 | 338 |
| W | 76 | 703 | 460 | >1000 | >1000 | 380 | 337 |
| X | 80 | 992 | >1000 | >1000 | >1000 | 624 | 338 |
| T | 30 | 656 | 361 | 659 | 383 | 607 | 320 |
| VC | 49 | 624 | 419 | 670 | 470 | 585 | 386 |

*= too few cells

Inhibition of TNF-α Production

Given the correlation of TNF-expressing macrophages with clinical AIDS-associated dementia, developing a method of controlling TNF-α levels provides a basis for managing this disease. WF-10, a compound comprising diluted tetrachlorodecaoxide (TCDO), substantially decreases the number of monocytes expressing TNF-α. Furthermore, WF-10 also significantly decreases the number of CD69+ monocytes. Since expression of CD69 and TNF-α discriminate monocytes from patients with dementia, the down modulation of those markers should be specific to AIDS dementia.

Figure 2:
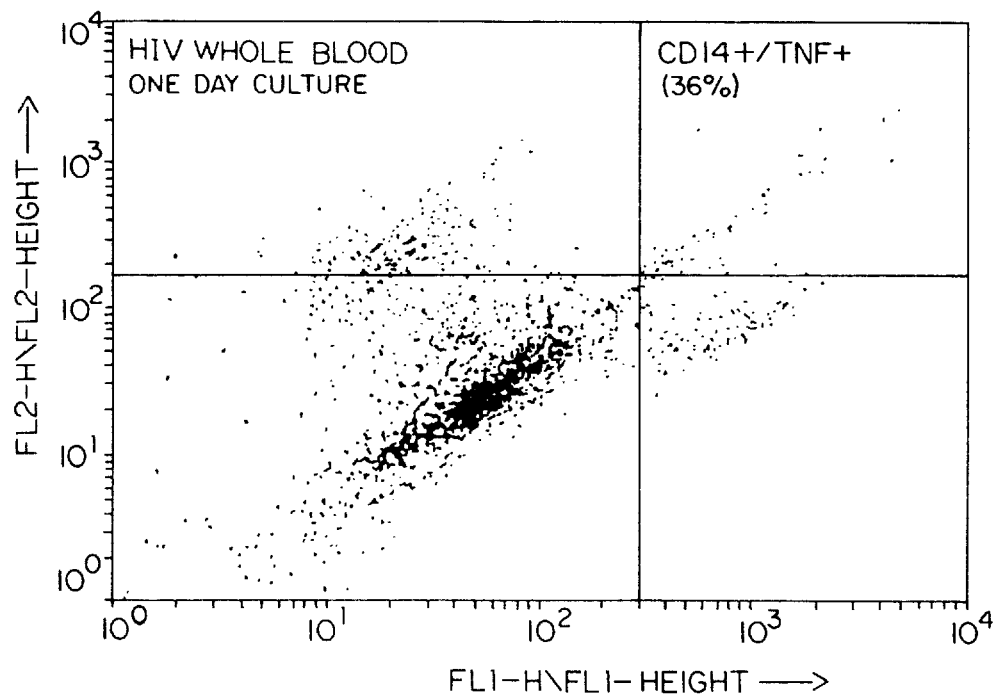
FIG. 2 is a dot plot showing percentages of cells expressing CD14 and TNF-α, with and without WF-10 treatment.
Figure 2:
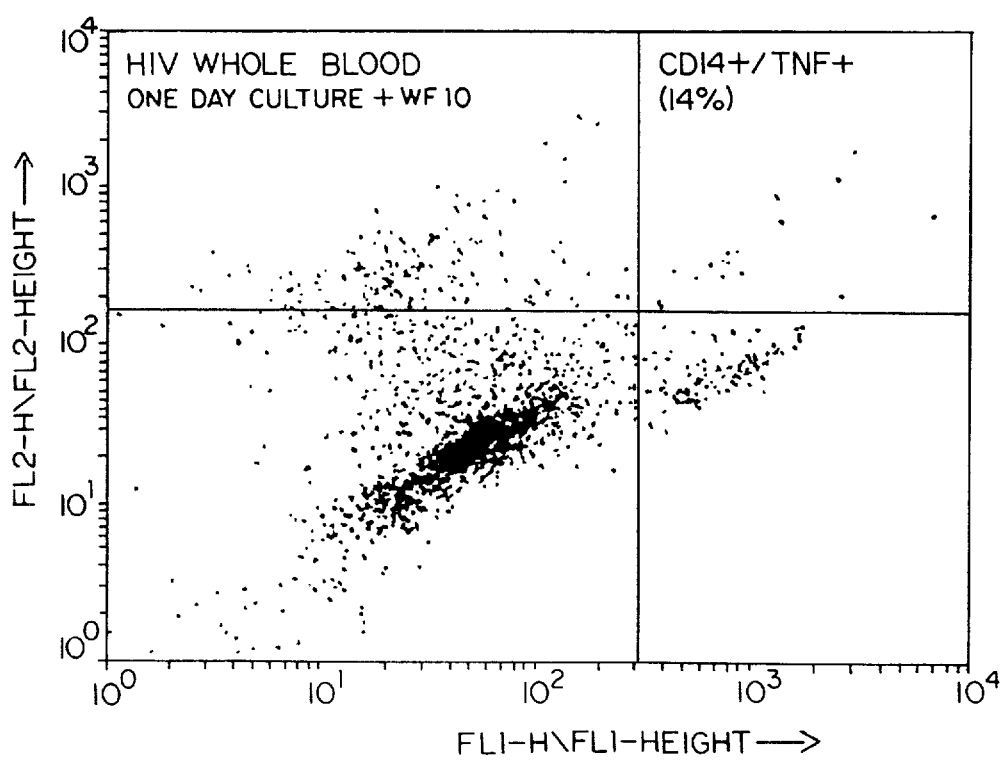
Figure 3:
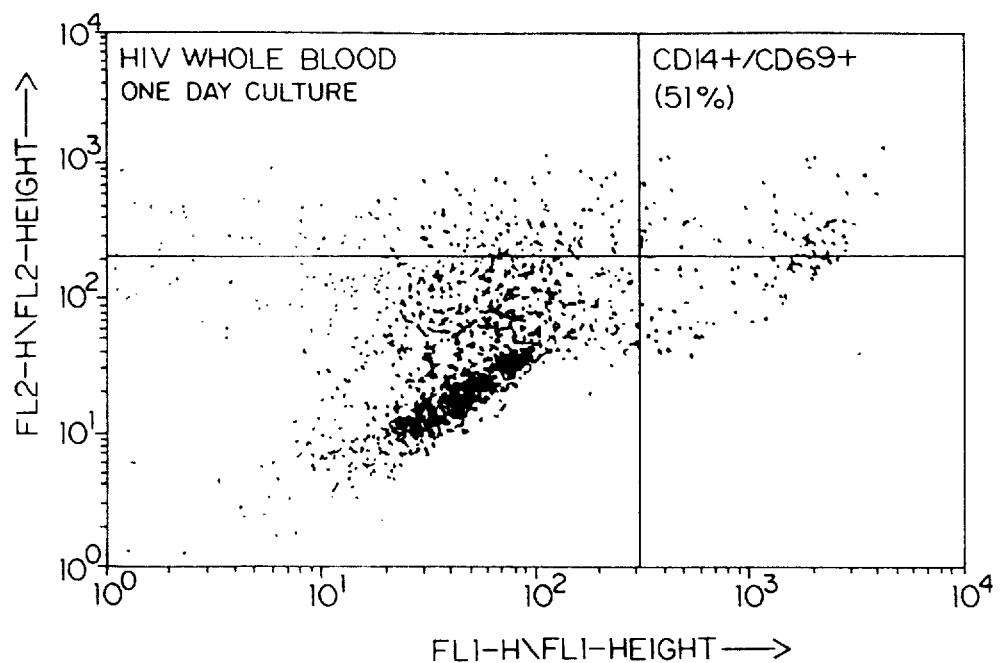
FIG. 3 is a dot plot showing percentages of cells expressing CD14 and CD69, with and without WF-10 treatment.
Figure 3:
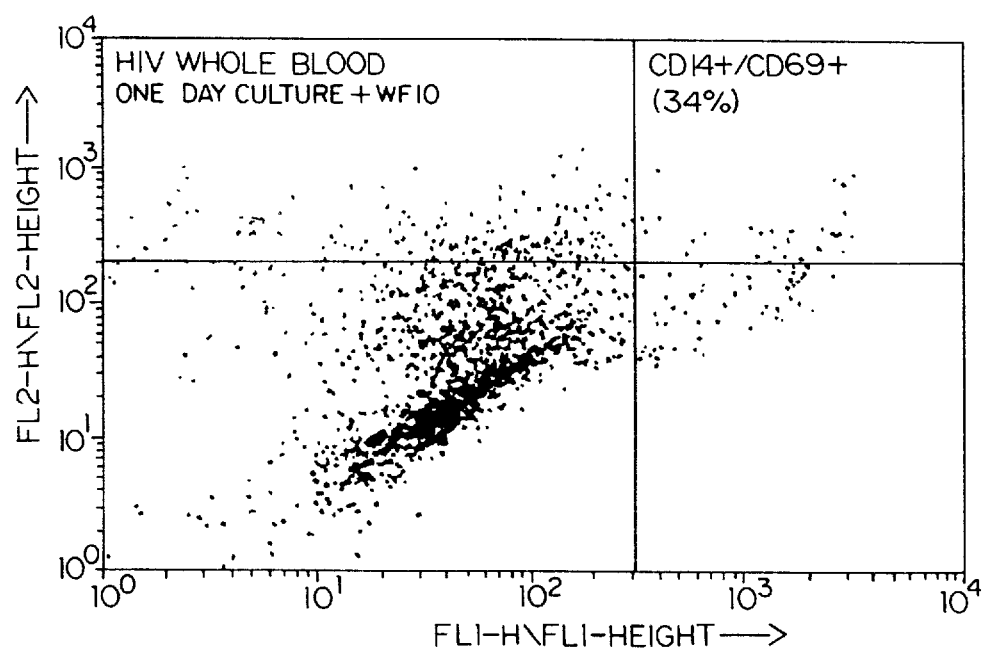

As shown in FIG. 2, the number of monocytes expressing TNF-α is decreased by approximately 61% after one day of culture with WF-10. Similarly, FIG. 3 shows that WF-10 decreases the number of CD69+ monocytes by approximately 33%. The experimental protocols were as follows. One ml of HIV+ whole heparinized blood was added to each of two polyvinyl tubes. WF-10 was added to one tube to a final dilution of 1/250 of concentrated stock. The tubes were incubated overnight at 37° C. One hundred μl aliquots were stained for CD14, CD16 and CD69 surface markers (Becton-Dickinson) for 20 min at RT. FacsLyse (Becton-Dickinson) was used to lyse the RBCs and was then removed by centrifugation at 400×g, 5 min. In the tubes to be stained for TNF-α expression, the cells were resuspended in 0.5 ml of permeabalizing solution (Becton-Dickinson) for 5 min at RT, then washed IX in PBS and the pellets resuspended in 0.1 ml of PBS. Anti-TNF-PE (R&D Systems, Inc., Minneapolis, Minn.) was added to each tube and allowed to react for 20 min at RT. All tubes were washed IX in PBS and the cells resuspended in PBS, containing azide and p formaldehyde.

TCDO comprises a stabilized activated oxygen in a chlorite ion matrix and is thought to activate the NADPH oxidase pathway. WF-10 has been used to protect patients from radiation therapy, to prevent post-operative infection and to treat sepsis. Further, TCDO has been shown to enhance phagocytic activity in macrophages. Accordingly, the finding that WF-10 suppresses expression of TNF-α, rather than promoting it, is absolutely unique.

Stabilized activated oxygen compounds useful in the practice of this invention are described in U.S. Pat. Nos. 4,507,285 and 4,725,437, which are hereby incorporated in their entirety by reference. WF-10 is available as Oxoferin (Oxo Chemie GmbH, Fort Worth, Tex.) but other formulations of TCDO are within the scope of this invention. Suitable doses will depend on the formulation of TCDO. A dose finding phase I/II study evaluating WF-10 administered intravenously and involving 48 patients established a maximum dose of approximately 0.5 ml/kg. Other suitable doses may be approximately 0.25 ml/kg. Preferably, a WF-10 regimen comprises 5 consecutive days of treatment every 3 weeks.

Inhibition of PDGF-B Production

Another potential mechanism for AIDS-associated dementia involves platelet derived growth factor B (PDGF-B). PDGF-B is a portion of the PDGF molecule (normally a dimer with another B molecule or with a PDGF-a molecule or an AA dimer) and is normally involved in the wound healing process. PDGF induces fibroblast cell proliferation, smooth muscle cell proliferation, and mesangial proliferation. In diseased tissues, it is typically produced by tissue-associated macrophages, which also express the PDGF-B receptor. In some studies, the macrophages within diseased tissue are proliferating. Therefore PDGF-B may act as an autocrine growth factor for macrophages as well as the previous described cells.

PDGF-B has been pathologically linked to various animal and human disease processes. Gamma interferon produced by lymphocytes from patients with tuberculosis induces PDGF-B expression in macrophages, a process that may account for fibrosis seen in the lungs of patients with TB. Similarly, expression of PDGF in kidneys with pathologic interstitial fibrosis is elevated in comparison to control kidneys. Transfection of a PDGF-B expression vector into rat kidneys caused glomerular sclerosis. PDGF-B is involved with kidney mesangial cells that express the PDGF-B receptor in an autocrine manner. These cells cause secondary proliferation of smooth muscle and endothelial cells as well as fibroblasts. These processes associated with PDGF-B are thought to be critical in inducing progressive renal disease. PDGF-B is also a critical growth factor in cardiovascular disease. In experimental models of arterial occlusion, PDGF-B is up regulated and drives smooth muscle and endothelial cell proliferation. Human atherosclerotic plaque has an abundance of PDGF-B expressing macrophages, cells that are also apparently proliferative.

Astrocytosis is the most common pathologic feature of AIDS dementia. Although astrogliosis is the normal brain response to injury, extreme astrogliosis in the form of an astrocytoma is driven by PDGF-B through both paracrine and autocrine type processes. In a rat model of brain injury response, PDGF-B was expressed in macrophages adjacent to the wound associated with astrocytosis. Astrocytoma cell lines have been shown to express PDGF-B as well as the PDGF-B receptor. FIG. 1 shows brain specimens from a patient with AIDS-associated dementia stained with both PDGF-B and PDGF-B receptor antibodies.

In four of six AIDS dementia brain specimens examined, the HIV integrated into the PDGF locus. This indicates that disruption of this locus may be responsible for the elaboration of PDGF-B by HIV transformed monocytes. In turn, this overabundance of PDGF-B may be a key factor in the astrocytosis associated with AIDS-associated dementia. WF-10 also may be shown to down regulate expression of PDGF. Accordingly, another embodiment of the invention is the method for treating AIDS-associated dementia by administering an amount of WF-10 sufficient to inhibit production of PDGF-B.

Although the invention has been described with respect to presently preferred embodiments, it should be recognized that various enhancements and modifications will be readily apparent to one of skill in the art and are within the scope of this invention.

What is claimed is:

1. A method for inhibiting expression of TNF-α in any patient having elevated levels of TNF-α, comprising the step of administering to a human an effective amount of a stabilized activated oxygen in a matrix of chlorite ions.

2. The method of claim 1, wherein the step of administering the stabilized activated oxygen comprises administering a pharmaceutically acceptable formulation of tetrachlorodecaoxide.

3. The method of claim 2, wherein the step of administering the stabilized activated oxygen comprises administering WF-10.

4. The method of claim 3, wherein the step of administering WF-10 comprises administering about 0.5 ml/kg.

* * * * *